United States Patent [19]

Ainsworth et al.

[11] 3,959,305
[45] May 25, 1976

[54] ACYLAMINO IMIDAZOLES

[75] Inventors: Anthony Trevor Ainsworth, Bishops Stortford; Carl John Rose, London, both of England

[73] Assignee: Beecham Group Limited, England

[22] Filed: Sept. 11, 1974

[21] Appl. No.: 504,962

Related U.S. Application Data

[62] Division of Ser. No. 337,062, March 1, 1973, Pat. No. 3,876,655.

[30] Foreign Application Priority Data

| Feb. 24, 1972 | United Kingdom | 8604/72 |
| Feb. 23, 1973 | United Kingdom | 9134/73 |
| Dec. 1, 1972 | United Kingdom | 55506/72 |

[52] U.S. Cl. ............................... 260/309; 424/273
[51] Int. Cl.² ................................ C07D 233/92
[58] Field of Search ............................... 260/309

[56] References Cited
OTHER PUBLICATIONS

Hoskinson Aust. J. Chem., 1968, Vol. 21, pp. 1913–1919.
Ichikawa et al., J. Heterocyclic Chem., 1965, Vol. 2, pp. 253–255.
Kulev et al., I. Chem. Abst., 1960, Vol. 54, column 11000.
Kulev et al., II Zhur. Obshchei Khim., 1959, Vol. 29, pp. 2401–2403.
Koroleva et al., Chem. Abst., 1962, Vol. 57, column 14594.
Montgomery et al., J. Org. Chem., 1959, Vol. 24, pp. 256–257.

*Primary Examiner*—Natalie Trousof

[57] ABSTRACT

Compounds of the formula (II):

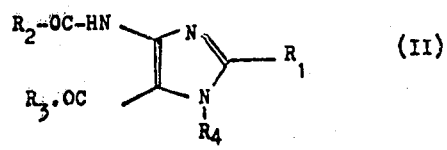

wherein $R_1$ is an aliphatic moiety of 1–12 carbon atoms, a cycloaliphatic moiety of 3–7 carbon atoms or said aliphatic moiety or said cycloaliphatic moiety substituted by halogen, carboxylic acid, esterified carboxylic acid, carboxamide, nitro, hydroxyl, etherified hydroxyl, acylated hydroxyl, amino, alkylamino, dialkylamino or acylated amino: $R_2$ is a hydrocarbon of 1–7 carbon atoms: $R_3$ is amino, lower alkylamino, di-lower alkylamino, anilino or lower alkoxyl; $R_4$ is hydrogen, $R_5$ or $CO.R_5$ wherein $R_5$ is a hydrocarbon of 1–7 carbon atoms, are useful for their anti-inflammatory activity.

13 Claims, No Drawings

ACYLAMINO IMIDAZOLES

This application is a divisional of application Ser. No. 337,062 filed Mar. 1, 1973 now U.S. Pat. No. 3,876,655.

This application relates to 5-acylamino-4-carboxamido-2-substituted imidazoles which compounds have been found to have beneficial anti-inflammatory activity.

Application Ser. No. 174,253, filed Aug. 23, 1971, which issued as U.S. Pat. No. 3,772,319 on Nov. 13, 1973, discloses the anti-inflammatory activity of certain imidazoles including inter alia those of formula (I):

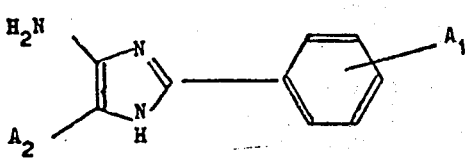

and its salts, wherein $A_1$ is hydrogen or halogen, carboxylic acid or an ester or amide thereof, nitro, trifluoromethyl, optionally substituted aryl, $C_{1-4}$ alkyl, hydroxyl or etherified or esterified hydroxyl, primary or secondary amino, acylated primary or secondary amino or tertiary amino and $A_2$ is optionally substituted phenyl or is carboxamido, carboxylic acid or an optionally substituted ester.

It has been confirmed that compounds within formula (I) have anti-inflammatory activity of varying degrees. Although we now believe that such activity is most likely to have clinical significance in cases wherein $A_2$ is carboxamido or lower ester and $A_1$ is hydrogen, halogen, nitro or methyl.

It has now been found that certain modification of an active group of the compounds (I) does not lead to loss of activity as might be expected, but can lead to a considerable enhancement in anti-inflammatory activity. The reason for the increase in activity is as yet uncertain. The present invention provides these compounds, each of which posses an acylated amino group on the imidazole ring.

Accordingly, the present invention provides compounds of the formula (II):

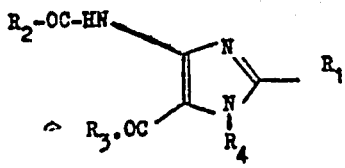

wherein $R_1$ is an aliphatic moiety of 1–12 carbon atoms, a cycloaliphatic moiety of 3–7 carbon atoms or said aliphatic moiety or said cycloaliphatic moiety substituted by halogen, carboxylic acid, esterified carboxylic acid, carboxamide, nitro, hydroxyl, etherified hydroxyl, acylated hydroxyl, amino, alkylamino especially lower alkylamino, dialkylamino especially di-lower alkylamino or acylated amino; $R_2$ is a hydrocarbon of 1–7 carbon atoms; $R_3$ is amino, lower alkylamino, di-lower alkylamino, anilino or lower alkoxyl; $R_4$ is hydrogen or a group $R_5$ or $CO.R_5$ wherein $R_5$ is a hydrocarbon of 1–7 carbon atoms.

Compounds of formula (II) wherein $R_4$ is hydrogen may exist in tautomeric forms. Such forms are included within this invention.

Compounds of formula (II) wherein $R_4$ is $R_5$ or $CO.R_5$ may exist in two or more isomeric forms. Such isomers are included within the invention.

Compounds of formula (II) may form solvates. Such solvates are preferably hydrates. Solvates of compound of formula (II) are included within the invention.

When used in this specification the term "hydrocarbon" means an aliphatic, cycloaliphatic, or aromatic group or combinations of such groups containing only carbon and hydrogen atoms. "Aliphatic" means a straight or branched chained group which may contain one or two carbon to carbon double or triple bonds. "Cycloaliphatic" means a carbon ring which when containing 6 carbon atoms may contain one or two carbon to carbon double bonds. "Aromatic" means phenyl or naphthyl. "Lower alkyl" means methyl, ethyl, propyl, or butyl. "Lower alkoxyl" means O-lower alkyl.

Suitable groups $R_2$ include methyl, ethyl, propyl, butyl, phenyl and benzyl. Methyl and ethyl are generally the more suitable groups $R_2$, the best activity usually being found when $R_2$ is methyl.

Suitable groups $R_3$ include amino, methylamino, dimethylamino, ethylamino, anilino, benzylamino, methoxyl, ethoxyl or propoxyl. Most suitably $R_3$ is amino, methylamino, anilino or ethoxyl, the best activity usually being found when $R_3$ is amino.

Suitable groups $R_4$ include hydrogen, $R_5$ and $CO.R_5$ wherein $R_5$ is methyl, ethyl or benzyl. Preferably $R_4$ is hydrogen. It is believed that the compounds of the invention having greatest anti-inflamatory activity are of formula (III):

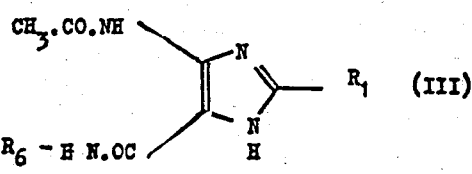

wherein $R_1$ is as previously defined and $R_6$ is hydrogen, methyl or phenyl, especially when $R_6$ is hydrogen.

We believe that a further particularly suitable group of compounds of the invention are those of formula (IV):

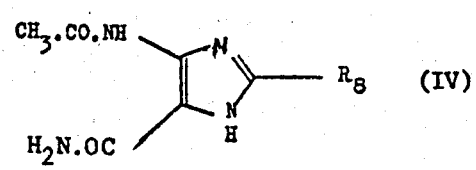

wherein $R_8$ is an aliphatic moiety of 1–6 carbon atoms, or a cycloaliphatic moiety of 3–7 carbon atoms.

Of the compounds of formula (IV), those of greatest activity include those wherein $R_8$ is ethyl, propyl, or isopentyl.

In a further aspect the invention provides a process for the preparation of compounds of general formula II which process comprises the acylation of a compound of formula (V):

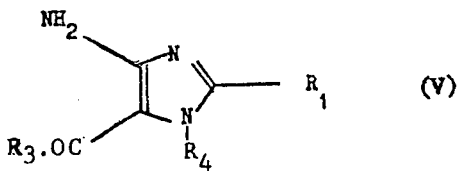

with an acylating derivative of an acid of general formula $HO.CO.R_2$, wherein $R_1$, $R_2$ and $R_3$ are as above defined.

By an acylating derivative of an acid $HO.CO.R_2$ is meant the acid itself or such derivatives as acid halides, (for example, the acid chloride or the acid bromide), the acid anhydride or a mixed anhydride, or a derivative made in situ by reaction with a dehydrating agent such as, for example, a carbodiimide such as dicyclohexyl carbodiimide. The reaction may be carried out by any conventional method of acylation.

Suitable solvents for the process include such solvents as halogenated hydrocarbons such as chloroform, methylene chloride and the like, polar solvents such as dimethylformamide or dimethylsulphoxide, basic solvents such as pyridine and the like, or any other such conventional solvent.

Low, ambient or high temperatures may be used depending upon the nature of the acylating agent, the group $R_2$ and the pH of the solution. For example, if an acid chloride $Cl.CO.R_2$ in pyridine is used, then the reaction would normally be carried out at ambient or low (e.g. $0°$ C) temperature; however if milder reagents such as the acid anhydride in chloroform were used, a high temperature, (e.g. reflux temperature) might be employed. In such reactions $R_4$ is generally hydrogen but it may also be a hydrocarbon group $R_5$, or less usually an acyl group $CO.R_5$.

If it is desired to form a compound wherein both the exocyclic and an endocyclic nitrogen atom is acylated the more severe acylating conditions listed above are, for example refluxing in pyridine for 2 hrs. with an anhydride. Representative acyl imidazoles of the present invention include:
5-Acetamido-4-carboxamido-2-methylimidazole.
5-Acetamido-4-carboxamido-2-ethylimidazole.
5-Acetamido-4-carboxamido-2-n-propylimidazole.
5-Acetamido-4-carboxamido-2-iso-propylimidazole.
5-Acetamido-4-carboxamido-2-butylimidazole.
5-Acetamido-4-carboxamido-2-n-hexylimidazole.
5-Acetamido-4-carboxamido-2-cyclohexylimidazole.
5-acetamido-4-carboxamido-2-cycohexenylimidazole.
5-Proprionamido-4-carboxamido-2-ethylimidazole.
5-Acetamido-4-ethoxycarbonyl-2-ethylimidazole.
5-Propionamido-4-methoxycarbonyl-2-ethylimidazole.

In a further aspect the invention provides a pharmaceutical composition comprising a compound of general formula (II) together with one or more pharmaceutically acceptable excipients, diluents or carriers.

The active compound may be present in the formulation as a salt or as the free base, either of which may be hydrated.

The compositions of the invention may be formulated in unit dosage forms to be administered orally (for example for pill, capsules, solutions, tablets and the like) parenterally (for example by injection of a solution in a sterile water) or by suppository. Such dosage forms will normally contain from 25 mgs. to 500mgs, and may be administered from, for example, 1 to 12 times daily, a suitable daily dose for a 70 kg adult being from 250–2500 mgs.

The compound of formula (V) may be prepared by a method similar to that reported in application Ser. No. 174253 and comprises the reaction of a nitrile of formula (VI) with a (capsules, solutions, tablets and the like) parenterally (for example by injection of a solution in a sterile water) or by suppository. Such dosage forms will normally contain from 25 mgs. to 500 mgs., and may be administered from, for example, 1–12 times daily, a suitable daily dose for a 70 kg adult being from 250–2500 mgs.

The compound of formula (V) may be prepared by a method similar to that reported in application Ser. No. 174253 and comprises the reaction of a nitrile of formula (VI) with a salt of a thioiminoether of formula (VII).

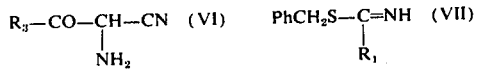

wherein $R_1$ and $R_2$ are as above defined. The following Examples serve to illustrate the invention.

EXAMPLE 1

5-Amino-4-carboxamido-2-methylimidazole

Methyl formamino benzylthioether hydrochloride (40 g) and aminocyanoacetamide (20 g) were refluxed in ethanol (120 ml) for 10 minutes. The resulting precipitate was filtered off and recrystallized from aqueous ethanol to give 5-amino-4-carboxamido-2-methyl imidazole as the hydrochloride (12 g.) m.p. $255°–260°$ C.

In an exactly analogous manner were prepared the hydrochlorides of 5-amino-4-carboxamido-2-ethylimidazole (m.p. $230°$ C ex. water), 5-amino-4-carboxamido-2-n-propylimidazole (m.p. $222°$ C ex. ethanol/ether), 5-amino-4-carboxamido-2-isopentylimidazole (m.p. $230°$ C–$240°$ C ex isopropanol), and 5-amino-4-carboxamido-2-carboxamidomethylimidazole (m.p. dec. ex acetone/water).

EXAMPLES 2–4

5-Acetamido-4-carboxamido-2-n-propylimidazole.

5-Amino-4-carboxamido-2-n-propylimidazole hydrochloride (4 g.) in pyridine (20 ml) was warmed with acetic anhydride (4 ml.) for ten minutes. On cooling a solid was obtained which on recrystallization from ethanol yielded 5-acetamido-4-carboxamido-2-n-propylimidazole (1.5g.), m.p. $183°$ C. In an exactly analogous manner were prepared 5-acetamido-4-carboxamido-2-methylimidazole (m.p. $278°$ C ex. aqueous acetone) and 5-acetamido-4-carboxamido-2-ethylimidazole (m.p. $233°–234°$ C ex. aqueous ethanol).

| COMPOUND | $ED_{50}$ (mg/kg) |
|---|---|
| 5-Acetamido-4-carboxamido-2-ethylimidazole | 100 |

What is claimed is:

1. A compound of the formula:

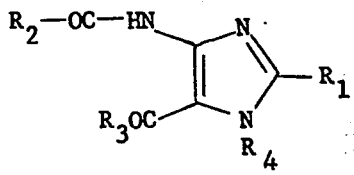

wherein
- $R_1$ is ethyl, n-propyl, isopropyl, butyl, isopentyl, n-hexyl, cyclohexyl or cyclohexenyl;
- $R_2$ is methyl or ethyl;
- $R_3$ is amino or alkoxy of 2 to 5 carbon atoms; and
- $R_4$ is hydrogen.

2. A compound according to claim 1 wherein $R_3$ is amino.

3. A compound according to claim 1 of the formula:

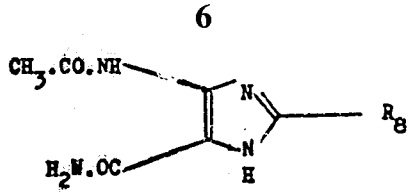

wherein $R_8$ is ethyl, propyl or isopentyl.

4. The compound according to claim 3 which is 5-acetamido-4-carboxamido-2-n-propylimidazole.

5. The compound according to claim 3 which is 5-acetamido-4-carboxamido-2-ethylimidazole.

6. The compound according to claim 3 which is 5-acetamido-4-carboxamido-2-isopropylimidazole.

7. The compound according to claim 1 which is 5-acetamido-4-carboxamido-2-butylimidazole.

8. The compound according to claim 1 which is 5-acetamido-4-carboxamido-2-n-hexylimidazole.

9. The compound according to claim 1 which is 5-acetamido-4-carboxamido-2-cyclohexylimidazole.

10. The compound according to claim 1 which is 5-acetamido-4-carboxamido-2-cyclohexenylimidazole.

11. The compound according to claim 1 which is 4-propionamido-4-carboxamido-2-ethylimidazole.

12. The compound according to claim 1 which is 5-acetamido-4-ethoxycarbonyl-2-ethylimidazole.

13. The compound according to claim 1 which is 5-propionamido-4-methoxycarbonyl-2-ethylimidazole.

* * * * *